United States Patent
Wigmore

(10) Patent No.: US 7,258,872 B1
(45) Date of Patent: Aug. 21, 2007

(54) CHROMONE ENTERIC RELEASE FORMULATION

(75) Inventor: Alexander James Wigmore, Derby (GB)

(73) Assignee: Thornton & Ross Limited, Huddersfield (GB)

( * ) Notice: Subject to any disclaimer, the term of this patent is extended or adjusted under 35 U.S.C. 154(b) by 793 days.

(21) Appl. No.: 09/831,681

(22) PCT Filed: Nov. 9, 1999

(86) PCT No.: PCT/GB99/03731

§ 371 (c)(1),
(2), (4) Date: May 10, 2001

(87) PCT Pub. No.: WO00/27392

PCT Pub. Date: May 18, 2000

(30) Foreign Application Priority Data

Nov. 11, 1998 (GB) ................................. 9824604.4

(51) Int. Cl.
*A61K 9/20* (2006.01)
*A61K 9/22* (2006.01)
*A61K 9/26* (2006.01)
*A61K 9/28* (2006.01)
*A61K 9/30* (2006.01)

(52) U.S. Cl. ...................... 424/464; 424/468; 424/469; 424/470; 424/474; 424/475; 424/489; 424/490

(58) Field of Classification Search ................ 424/464, 424/465, 468, 469, 470, 474, 489, 490
See application file for complete search history.

(56) References Cited

U.S. PATENT DOCUMENTS

| 4,067,992 A | 1/1978 | Kingsley et al. | |
| 4,232,012 A | 11/1980 | Orr et al. | |
| 6,200,602 B1 * | 3/2001 | Watts et al. | 424/463 |

FOREIGN PATENT DOCUMENTS

| DE | 9900116 | 1/1999 | |
| EP | 0502092 | 9/1992 | |
| GB | 1423985 | 2/1976 | |
| GB | 1525294 | 9/1978 | |
| GB | 1549229 | 7/1979 | |
| GB | 1569612 | 6/1980 | |
| GB | 1595220 | 8/1981 | |
| GB | 2086227 | 5/1982 | |
| GB | 2 324 962 A | * 11/1998 | |
| WO | WO85/00015 | 1/1985 | |
| WO | WO94/28911 | 12/1994 | |
| WO | WO98/51300 | 11/1998 | |

OTHER PUBLICATIONS

D. Kumar, "Gastric Motor Physiology and Pathophysiology"—The Stomach—Churchill Livingstone, London (1992) pp. 129-142.
L. Businco et al, "Evaluation of the Efficacy of Oral Cromolyn Sodium or an Oligoantigenic Diet in Children with Atopic Dermatitis: A Multicenter Study of 1085 Patients"—J Invest Allerg Clin Immunol—6(s), 103-109 (1996).
A. C. DeGroot et al., "Contact Allergy to Cocamidopropyl Betaine"—Contact Dermititis—33(6), 419-156 (1995).
G.F. Moss et al., "Plasma Levels and Urinary Excretion of Disodium Cromoglycate After Inhalation by Human Volunteers"—Toxicol &Appl Pharm_20, 147-156 (1971).
. Horowitz et al., "Changes in Gastric Emptying Rates with Age"—Clinical Science 67, 213-218 (1984).
Fimmel et al. "Long-Term Ambulatory Gastric pH Monitoring: Validation of a New Method and Effect of $H_2$- Antagonists"—CASTROENTEROL—88, 1842-1851, (1985).
E.J. Prewett, et al., "Twenty-Four Hour Intragastric Acidity and Plasma Gastrin Concentration Profiles in Female and Male Subjects"—Clinical Science—80, 619-624 (1991).
J.R. Malagelada et al., "Measurement of Gastric Functions During Digestion of Ordinary Solid Meals in Man"—GASTROENTEROL—70, 203-210 (1976).
U. Bengtsson et al., "IgE-Positive Duodenal Mast Cells in Patients with Food-Related Diarrhea"—Int Arch Allergy Appl Immunol—95, 86-91 (1991).
L.J. Miller et al., "Postprandial Duodenal Function in Man"—GUT—19, 699-706, (1978).
J-R Malagelada et al., "Quantification of Gastric Solid-Liquid Discrimination During Digestion of Ordinary Meals"—GASTROENTEROL—72, 1264-1267 (1977).

* cited by examiner

*Primary Examiner*—S. Tran
(74) *Attorney, Agent, or Firm*—Haugen Law Firm PLLP

(57) ABSTRACT

Orally administered chromones have been found to be effective in the treatment of allergic conditions such as asthma, general food allergies, ulcerative colitis, atopic eczema, chronic urticaria, and irritable bowel syndrome if it is presented such that the respective chromone becomes bioavailable within ten minutes of exposure to an intestinal fluid.

13 Claims, No Drawings

CHROMONE ENTERIC RELEASE FORMULATION

The present invention relates to the treatment of allergic conditions, in particular allergic conditions which relate to the nature of the food or drink consumed by the patient. Allergy to ingested substances can manifest itself in a wide range of symptoms affecting any organ in the body. Commonly it affects particularly the gastrointestinal tract, the skin, the lung, the nose and the central nervous system. Allergic reactions to ingested substances affecting these organs can manifest themselves as abdominal pain, abdominal bloating, disturbance of bowel function, vomiting, rashes, skin irritation, wheezing and shortness of breath, nasal running and nasal blockage, headache and behavioural changes. In addition, in severe food allergic reactions, the cardiovascular and respiratory systems can be compromised giving anaphylactic shock and in some cases death.

It is also recognised that in certain chronic diseases, allergy to ingested substances is the probable cause of the disease in a proportion of patients. These diseases include anaphylactic shock, atopic dermatitis, chronic urticaria, asthma, allergic rhinitis, irritable bowel syndrome, migraine and hyperactivity in children. It is also possible that food allergy is a factor in certain patients with inflammatory bowel disease (ulcerative colitis and Crohn's disease).

This vast array of symptoms and diseases presents the medical practitioner with tremendous problems of diagnosis and management. In the absence of any reliable tests for food allergy other than double-blind, placebo-controlled, food challenges which are time-consuming, expensive and potentially dangerous, many practitioners are often reluctant to regard allergy as the cause, and rely on symptomatic treatment for management. For example, wheezing and asthma are treated with bronchodilators, atopic dermatitis with topical corticosteroids, rhinitis with nasal decongestants and irritable bowel syndrome with anti-spasmodics.

One drug which has been investigated over the years for treating allergic conditions, particularly asthma, is sodium cromoglycate. This was initially launched in the 1960's by Fisons as an inhaled prophylactic treatment for asthma. In 1972, an insufflated powder formulation "Rynacrom" was introduced for nasal allergies, followed in 1975 by a more convenient nasal spray solution. In 1976, a dropper bottle solution called "Opticrom" was launched for eye allergies and, in 1978, an oral powder ("Nalcrom") was marketed initially for the treatment of inflammatory bowel disease and later for food allergy. These names are all registered trademarks. However, various clinical studies have failed to confirm that the oral formulation of sodium cromoglycate is adequately effective in inflammatory bowel disease and this indication was withdrawn in the early 1980's.

The clinical efficacy of oral sodium cromoglycate (Nalcrom) has been reported as being variable with some authorities reporting good effects and others variable or poor effects.

The current "Nalcrom" formulation of sodium cromoglycate consists of a powder which is either taken by the patient as a solution (ie after dissolving the powder in water) or presented in a gelatin capsule which dissolves in the stomach. As one would expect, the various Fisons patent specifications concerning sodium cromoglycate list a vast number of theoretical formulations of the drug, practically none of which have been put into effect. Thus, GB 1 423 985 discloses an enteric coated composition intended to make the drug available "at an appropriate part of the gastrointestinal tract" (unspecified) and GB 1 549 229 discloses a gelatin capsule containing granules of the drug, for oral use in the treatment of allergic conditions. Both of these two patent documents date from the 1970's and there is no indication that the performance of these compositions in practice was investigated.

The previously proposed powder or gelatin capsules of sodium cromoglycate are, we consider, of low bioavailability because the sodium salt of the drug is converted in the acidic conditions of the stomach into insoluble and inactive cromoglycic acid. Although, in the alkaline medium of the duodenum, the cromoglycic acid may convert back to a salt, this is unlikely to be the sodium salt and is more likely to be an insoluble and inactive salt such as a calcium salt. The enteric-coated formulations which have been proposed previously, at least on paper, similarly may be of low bioavailability because the sodium cromoglycate is released from the enteric coating into the duodenum in a lump that does not dissolve, rather than being dispersed evenly throughout the food material passing through the small intestine. A gel may form round the lump of sodium cromoglycate on exposure to aqueous liquid that inhibits dispersion of the sodium cromoglycate. The gel may seal the surface of the sodium cromoglycate, preventing further wetting of sodium cromoglycate remaining inside the gel.

We have now investigated the matter more closely and we have found that chromones such as sodium cromoglycate are effective in treating these various allergic conditions providing that they are formulated in a particular manner. In addition, the patient may first be selected according to a specific criterion.

A first aspect of the invention provides an oral drug delivery composition comprising a chromone wherein (1) not more than 10%, preferably not more than 5%, of the chromone dissolves after thirty minutes, one, two, three or five hours exposure of the composition to simulated gastric fluid and (2) from 15 to 90%, preferably from 20, 30, 40, 50, 60, 70, 80 or 90 to 95% or 100% of the chromone dissolves within 10, or preferably about 1, 2, 3, 4, 5, 6, 7, 8 or 9, or less preferably about 15, 20, 25 or 30, minutes of subsequent exposure of the composition to simulated intestinal fluid.

The oral drug delivery composition may be made bioavailable in the small intestine following human oral administration. The term "oral drug delivery composition" does not include inhaled drug delivery compositions.

It is preferred that at during and at the end of exposure of the composition to the simulated gastric fluid as indicated, at least 50, 60, 70, 80, 90, 95 or 100% of the chromone comprised in the composition is not in contact with the simulated gastric fluid. For example, it is preferred that the composition comprises an enteric coating which acts substantially to prevent contact between the simulated gastric fluid and the chromone.

The simulated intestinal fluid may comprise heavy metal or alkaline earth metal ions, ie ions of metals in group IIa, Ib, IIIa, IVa or IVb of the periodic table, for example $Ca^{2+}$, $Mg^{2+}$, $Pb^{2+}$, and/or in particular $Fe^{3+}$, $Fe^{2+}$ or $Zn^{2+}$. The metal ion or ions, preferably $Ca^{2+}$ and/or $Mg^{2+}$ may be present in individual concentrations between about 0.22 ppm and about 200 ppm, for example between about 1 and 100 ppm or between about 2 and 20 ppm, preferably about 15 ppm. The metal ion or ions may be present in concentrations similar to those that may be found in the human small intestine. Alternatively, the metal ion or ions (preferably all heavy metal ions as defined above, or at least $Ca^{2+}$, $Mg^{2+}$, $Pb^{2+}$, $Fe^{3+}$, $Fe^{2+}$ and $Zn^{2+}$) may be substantially absent, for example present in individual concentrations below about 0.22 ppm.

We consider it to be desirable for the drug to be applied evenly and preferably temporally consistently across the surface of the mucosa in the small intestine prior to and at the same time as the surface of the mucosa is exposed to the food which is causing the allergy. However, we consider that the maximum concentration of sodium cromoglycate to which the mucosa is exposed may be more important than the cumulative (ie time×concentration) exposure. Thus, low concentrations (for example, less than 0.05% w:v) of chromone may be biologically ineffective even if applied to the mucosa over a prolonged period. "Intal" nebuliser solution (registered trade mark), for example, is used at a chromone concentration of 1% and Rynacrom, Lomusol and Opticrom are used at a chromone concentration of 2% or (in some cases) 4%. We consider it may be beneficial to achieve a concentration of at least 0.05%, preferably 0.1%, 0.2%, 0.5%, 1%, 2% or 4% (w:v) at the mucosal surface (for example of the small intestine), preferably at least 2 to 4 times a day, or at the same time as or before exposure to allergen, of a chromone such as sodium cromoglycate (scg).

Calculations of concentrations of scg that may be achieved in the gut, for example in the small intestine, by present formulations of scg are discussed in Example 5. Previous formulations may achieve a maximal concentration of less than 0.04% w:v.

Thus, the composition may achieve a concentration of at least 0.05%, preferably 0.06%, 0.07%, 0.09%, 0.1%, 0.11%, 0.12%, 0.13%, 0.14%, 0.15%, 0.16%, 0.17%, 0.18%, 0.19%, 0.2%, 0.5%, 1%, 2% or 4% (w:v) of chromone under the following conditions. The composition is added to 190 ml of simulated gastric fluid (discussed further below) and incubated for 2 hr at 37° C. After gentle swirling, an aliquot of 5, 10, 15, 50, 100 or 150 ml (preferably 5 ml) is withdrawn. The pH of the aliquot is adjusted to a pH of 7.5, 6.5 or 5.5 (preferably 7.5) by the addition of sodium hydroxide. The mixture is incubated at 37° C. for 1, 2, 3, 4, 5, 6, 7, 8, 9, or 10 minutes with gentle swirling. The concentration of chromone in the fluid is then measured, as described below. Alternatively, the aliquot is mixed by gentle swirling with 5, 10, 15, 50, 100 or 150 ml (preferably 5 ml) of simulated intestinal fluid (discussed further below; pH 7.5, 6.5 or 5.5, preferably 7.5) at 37° C. Incubation at 37° C. and measurement of the concentration of chromone is carried out in the same way. If the composition is still in the form of a tablet or capsule at the end of the exposure of the composition to simulated gastric fluid, then the aliquot includes the tablet or capsule.

It is preferred that the composition is in the form of a tablet or capsule (comprising the chromone). It is further preferred that the composition is in the form of a tablet or capsule (comprising the chromone) at the end of the incubation in simulated gastric fluid. It is still further preferred that the tablet or capsule comprises between about 10, 20, 30, 40, 50, 60, 70, 80, 90 or 100 and about 500, 400, 300, 200 or 150 mg of chromone, preferably between about 50 and 200 mg of chromone, most preferably about 100 mg of chromone. The tablet or capsule may be enteric coated, as discussed further below.

We consider that it is beneficial that the chromone is made bioavailable as rapidly as possible on entering the small intestine following human oral administration (ie preferably within the first 10 minutes of the composition being exposed to intestinal fluid). This may have the benefits of making the chromone bioavailable in a smaller volume of the intestinal contents than if release is slower (ie occurs over longer than a 10 minute period), thus achieving a higher local concentration of the chromone, particularly if the chromone is comprised in a tablet or capsule as set out above when it enters the small intestine. Successive portions of the small intestine may be exposed to the chromone as the intestinal contents into which it was released progress along the small intestine. Further, we consider that it may be particularly beneficial that substantially all of the chromone is made bioavailable within the duodenum (the first approximately 25 cm of the small intestine) such that the entire jejunum (ie the portion of the small intestine following the duodenum, of approximately 3 m in length) is exposed to the maximum concentration of chromone. The jejunum may be the most important portion of the small intestine in relation to allergic conditions relating to ingested substances, as discussed below, and therefore we consider that it may be the most important portion to expose to a chromone.

Chromones such as sodium cromoglycate are poorly absorbed in the gut. Less than 1% of ingested sodium cromoglycate may be absorbed during passage through the gut (see, for example, Moss et al (1971) *Toxicol & Appl Pharmacol* 20, 147-156; Walker et al (1972) *J Pharm Pharmac* 24, 525-531). Chromones are also not significantly metabolised in the gut (see for example Moss et al (1971) and Walker et al (1972), above). Thus, the concentration of chromone in the small intestine is unlikely to be altered significantly by uptake or metabolism of the chromone following release of the chromone. Mixing of the intestinal contents may reduce local concentration. Net absorption of fluid from the small intestine may increase the concentration of chromone, as described in the references mentioned in Example 5. Thus, the concentration in the upper jejunum may be approximately double that in the mid-duodenum. Pancreatic and biliary secretion into the small intestine may reduce the concentration of chromone in later sections of the intestine.

As only a small proportion of chromone is removed from the small intestine by absorption or metabolism, early release of the chromone in the small intestine, as described herein, may be preferable to release of the chromone in more than one section of the small intestine, as it may maximise the concentration of chromone to which the mucosa of the small intestine is exposed.

The chromone is preferably (sodium) cromoglycate or nedocromil (sodium). References to sodium cromoglycate hereafter refer to the class of chromones as well as to the individual compound.

The composition may be formulated, for example, as a tablet or capsule or as a unit dose that may be suspended in a liquid immediately prior to use. The tablet or capsule may have an enteric coating. The enteric coating (and the capsule, if appropriate) may dissolve or disintegrate, preferably rapidly (ie in less than 10 minutes), when it reaches alkaline conditions, for example on entering the small intestine.

Less preferably, the tablet or capsule may not have an enteric coating but may disintegrate in the stomach to release an enteric coated composition comprising sodium cromoglycate. Similarly, the suspendible unit dose formulation may comprise an enteric coated composition comprising sodium cromoglycate.

It may be preferred that if the formulation is a capsule it is not an enteric coated capsule. This is because the requirement for disintegration of both an enteric coat and a capsule may result in slower exposure of the composition comprising sodium cromoglycate to the intestinal fluid than may be achieved with a enteric coated tablet formulation.

A drug can be made "bioavailable" or soluble, for example, either as a result of the coating disintegrating or as a result of the coating becoming porous, followed by dispersal and dissolution of the drug. Preferably, the coating disintegrates. For a chromone, as discussed above, dispersal and dissolution of the drug may require that the chromone is rapidly dispersed on exposure to an aqueous environment, for example intestinal fluid, or that the chromone is exposed to the aqueous environment in small aliquots that are not big enough for a non-dispersible gel to form. Thus, when the chromone is formulated with a larger mass of disintegrant, for example microcrystalline cellulose in a ratio of 2.5:1 to the chromone, the disintegrant may promote rapid disintegration of the tablet before a gel has formed. When the chromone is formulated as enteric coated pellets of less than 5 mm diameter, preferably less than 1.5 mm diameter, the surface area:mass ratio of the chromone exposed to the aqueous environment in each pellet may be sufficiently high that the chromone disperses and dissolves rather than forming a gel. Thus, release of a chromone from an enteric coated dry formulation requires disintegration or porosity of the coating and dispersal and dissolution of the chromone.

When the composition comprises a said pellet, it is preferred that the composition is such as to prevent release of the sodium cromoglycate from said pellet in gastric fluids, but to permit release (including dispersion and dissolution) of the sodium cromoglycate from said pellet in intestinal fluids, preferably within 10 minutes of exposure to the intestinal fluids.

The rate may be measured in vitro as a dissolution rate of said unit in simulated gastric and intestinal fluids, when measured in a flow through cell (eg Sotax Dissotest CE6 (Sotax AG, Basel, CH4123 Allschwil 1, Switzerland), equipped with 12 mm cells) at 8 ml/min and 37° C. Typically, (a) not more than 10%, preferably not more than 5%, of the total sodium cromoglycate is released after two, three or five hours in simulated gastric fluid (eg USP, pH1.2, without enzymes, for example USP XXIII, page 2053, available from Sigma-Aldrich Company Ltd, Fancy Road, Poole, Dorset, BH12 4QH, UK; catalogue number G8285) in said assembly, (b) from 15 to 90%, preferably from 20 to 95% or 100%, of the total sodium cromoglycate is released after two hours, 1 hour, 30 minutes or preferably 10, 9, 8, 7, 6, 5, 4, 3, 2, or 1 minutes or 30 seconds, in simulated intestinal fluid (eg USP, pH 7.5, without enzymes, for example USP XXIII) in said assembly.

Alternatively, the pH of the simulated intestinal fluid may be pH 6.5 or 5.5. A Sotax™ CE70 apparatus may be used in place of a Sotax™ CE4 apparatus. If appropriate, any of the following Sotax™ cell types may be used in place of the 12 mm tablet cell: tablet cell 22.6 mm; cell suitable for powders and granules; cell suitable for implants; or a cell suitable for suppositories and soft gelatine capsules. The method and apparatus used may conform to method USP4. The Sotax™ CE70 apparatus, for example conforms to USP4. Flow-through dissolution methods, such as USP4 methods, are suitable for extended release and poorly soluble products. In the Sotax™ CE 70 apparatus, for example, the test sample is located in a small-volume cell through which the test solvent (ie the simulated gastric or intestinal fluid) passes at a temperature of 37° C. The fluid flow may be directed through a porous glass plate or a bed of beads in order to produce a dispersed flow of solvent. Turbulent or laminar flow can also be achieved by changing the bottom barrier. The eluate is filtered on leaving the cell and can be analysed directly or collected in fractions.

The concentration of a solution of a chromone, for example sodium cromoglycate, may be measured by measuring the absorbance of the solution at 326 or 325 nm, or by chromatography, for example high performance liquid chromatography (HPLC), techniques, as is well known to those skilled in the art. Thus, these techniques may be used to analyse the eluate and thereby measure the rate and extent to which the chromone enters solution from (ie is released from) a composition of the invention.

As indicated above, the simulated intestinal fluid may comprise a heavy metal ion. Preferences in relation to the concentration and nature of such a heavy metal ion are as indicated above in relation to an earlier aspect of the invention.

The limiting factor in making a chromone bioavailable from an enteric release formulation may be the dispersion of the formulation and the dissolution of the chromone once the enteric coating has disintegrated or become porous (preferably disintegrated).

This may be measured by exposing the formulation without enteric coat (ie before the enteric coat is applied) to an aqueous buffer or to simulated intestinal fluid and observing the behaviour of the formulation and/or the degree of solubilisation of the chromone.

Thus, the tablet or pellet may be placed in 30 ml of distilled water at 20° C. and prodded at various time intervals. On prodding, the tablet or pellet may remain intact or may disintegrate. It is preferred that the tablet or pellet disintegrates on prodding after (in order of preference) 10, 9, 8, 7, 6, 5, 4, 3, 2, or 1 minute or 30 second exposure to the liquid. It is particularly preferred that the tablet or pellet disintegrates on prodding after less than 2 minutes' exposure to the distilled water.

It may be found that if a formulation, particularly a tablet, comprising a chromone does not disintegrate after 1 or 2 minutes exposure, that it is very unlikely to disintegrate after further exposure, even for several hours. This may be because, if a chromone gel is able to form in the first few minutes, this may hold the tablet together.

It will be appreciated that when sampling, the liquid containing the tablet(s) or pellet(s) under test should be mixed in a standardised way, which should be sufficient to ensure homogeneity of the liquid, but not so vigorous as to lead to disintegration of the tablet or pellet. Suitably, the sample liquid may be gently swirled for 10 seconds at minute intervals, prior to removal of an aliquot for assay.

It is preferred that at least 50%, 60, 70, 80 or 90% of the chromone has entered solution after 10, 9, 8, 7, 6, 5, 4, 3, 2 or 1 minute exposure to distilled water at 20° C. in a volume of 30 ml.

In an embodiment of the first aspect of the invention, the oral drug delivery composition further comprises disintegrant at a ratio of at least 1.2, preferably at least 1.3 or 1.4, more preferably at least 1.5:1 (w:w) of disintegrant to chromone.

A second aspect of the invention is an oral drug delivery composition comprising a chromone wherein the composition further comprises disintegrant at a ratio of at least 1.2, preferably at least 1.3 or 1.4, more preferably at least 1.5:1 (w:w) of disintegrant to chromone. Preferably, the chromone is made bioavailable in the small intestine following human oral administration and/or the composition has the other properties described above.

The following preferences apply to both the above aspects of the invention.

It is preferred that the ratio of disintegrant to chromone is at least 1.3:1, 1.4:1, 1.5:1, 2:1, 2.5:1, 3:1, 4:1 or 5:1. Ratios are expressed as weight:weight ratios. It is preferred that the ratio of disintegrant to chromone is less than about 20:1, 15:1, 10:1, 8:1 or 5:1. The higher the ratio of disintegrant to chromone, the better the disintegration properties of the composition may be, but also the greater the mass of composition that may be required to deliver a particular mass of chromone. Thus, a balance may be required between improving disintegration and minimising the mass of composition that has to be administered to a patient.

It is preferred that the chromone and the disintegrant together form at least 30%, 40%, 50%, 60%, 70%, 80%, 90% or 95% (by mass) of the mass of the composition, for example in the form of a tablet. It is preferred that the remainder of the mass of the composition consists of materials forming an enteric coat and/or surfactant, as discussed below.

In a particularly preferred embodiment, the ratio of disintegrant to chromone may between about 1.4:1 and 2.5:1. When the ratio of disintegrant to chromone is less than 2.5:1, for example 1.5:1, it is preferred that the composition further comprises a surfactant, as discussed below.

In the disintegration/solubilisation assay described above, the gentle swirling may be sufficient to produce after 1 or 2 minutes' exposure to water a "snow-storm" type appearance with a tablet comprising 261 mg of the disintegrant microcrystalline cellulose and 100 mg sodium cromoglycate granules, as described in Example 1.

The term "disintegrant" is well known to those skilled in the art, as discussed in Remington's: "The Science and Practice of Pharmacy", 19th Edition. A disintegrant is a substance or mixture of substances that may be added to a pharmaceutical tablet in order to facilitate its breakup or disintegration after administration, or in an in vitro test designed to assess the disintegration of a tablet (as described above or as also described in Remington's: "The Science and Practice of Pharmacy", 19th Edition). Disintegrants may be grouped as starches, clays, celluloses, algins, gums and cross-linked polymers.

Examples of disintegrants that may be used in the present invention include corn and potato starch, Veegum HV, methylcellulose, agar, bentonite, cellulose and wood products, natural sponge, cation-exchange resins, alginic acid, guar gum, citrus pulp and carboxymethylcellulose. Croscarmelose (a cross-linked cellulose), crospovidone (a cross-linked polymer), sodium starch glycolate (a cross-linked starch) and cross-linked PVP have been termed superdisintegrants as they are typically effective at 2 to 4% of a tablet composition. Acdisol is a further example of a superdisintegrant.

It will be appreciated that one or more than one disintegrant may be used in a composition of the invention. The ratio cited above of disintegrant to chromone is the ratio of total disintegrant to chromone.

A preferred disintegrant is microcrystalline cellulose. Particularly preferred forms of microcrystalline cellulose include Avicel, in particular Avicel PH101 or PH102 (FMC Corporation, Pharmaceutical Division, 1735 Market Street, Philadelphia, Pa. 19103). Avicel PH301 and PH302 (from the same supplier) are slightly denser than Avicel PH101 and PH102 and may also be preferred, for example in capsule formulations.

It is preferred that a superdisintegrant as listed above is not used as the sole disintegrant in the ratios given above, as a superdisintegrant may itself form a gel which may retard dispersal of the composition. However, a superdisintegrant may be used in a composition of the invention in combination with a disintegrant which is not a superdisintegrant, for example microcrystalline cellulose. Thus it is preferred that a superdisintegrant does not comprise more than 20, 30, 40, 50, 60, 70 or 80% of the mass of the formulation.

It will be appreciated that in the prior art, disintegrants are routinely used at only up to about 20% of the weight of a tablet. In a typical tablet of the invention in which the enteric coat constitutes about 10% of the mass of the tablet and the remainder of the tablet is composed of disintegrant and chromone, a ratio of disintegrant to chromone of 1.5:1 would mean that the disintegrant constitutes about 54% of the mass of the tablet. A ratio of disintegrant to chromone of 2.5:1 would mean that the disintegrant constitutes about 65% of the mass of the tablet. It will further be appreciated that, as set out in, for example, GB 1 549 229, the preference in the art has been to formulate sodium cromoglycate in the substantial absence of excipients, such as disintegrants.

Whilst not intending to be bound by theory, it is considered that the disintegrant may aid bioavailability of the chromone by aiding its dispersion and/or dissolution on exposure to the intestinal contents. The disintegrant may swell on exposure to aqueous liquid and help disperse the chromone. Microcrystalline cellulose, for example, swells dramatically on exposure to aqueous liquid, for example water. It is considered that in the absence of disintegrant in a ratio of at least 1.2:1, 1.5:1, 2.0:1 or 2.5:1 (w:v) disintegrant:chromone, the chromone may form a gel on exposure to aqueous liquid that inhibits dispersion of the chromone. The gel may seal the surface of the chromone, preventing further wetting of chromone remaining inside the gel. In comparison, with compositions of the invention, the enteric coated tablet may enter the duodenum, the enteric coat dissolve and the tablet disintegrate rapidly to release and disperse the chromone, which may then dissolve.

The chromone may be granulated before being mixed with the disintegrant, for example microcrystalline cellulose. A lubricant, for example magnesium stearate, as is well known to those skilled in the art, may be added. Further examples of lubricants may be given in Remington supra and in Martindale: The Extra Pharmacopoeia, $32^{nd}$ edition. A tablet may then be formed from the granules and disintegrant, using methods well known to those skilled in the art, and as described in Example 2. The ratio of disintegrant to chromone granules in the tablet may be 2.5:1, or 1.5:1, particularly when a surfactant is added to the chromone, as discussed below. As is known to those skilled in the art and as described in Remington supra, the pressure employed in tabletting may affect the dispersal of the tablet and may require adjustment depending on the excipients used.

The granules may be of 25 to 250 µm, 25 to 500 µm, 200 to 1100 µm, or 100 to 750 µm diameter. These figures preferably refer to at least 50%, preferably at least 75%, 90%, 95%, 99% and most preferably 100% of the granules in the formulation. A median particle diameter of about 200 µm may be preferred.

The chromone may be granulated by known techniques, for example using a wet granulation method, as described in Examples 1 or 2. It will be appreciated that a diluent may be added to the chromone to aid fluidisation during granulation. The diluent may be a disintegrant. For example, microcrystalline cellulose may be used as a diluent during granulation, for example at about 10% of the weight of the chromone. Any disintegrant used as a diluent is included as disintegrant when calculating the ratio of disintegrant to chromone.

A surfactant may be added to the chromone, for example during granulation, as described in Example 2. It is preferred that the surfactant is an amphoteric surfactant or a nonionic surfactant. It is strongly preferred that the surfactant is not an anionic or cationic surfactant, terms well known to those skilled in the art (see, for example, Martindale, supra). An anionic surfactant (for example sodium lauryl sulphate)

dissociates in aqueous solution to form an anion, which is responsible for the surface activity, and a cation (which is generally smaller than the anion) which is devoid of surface-active properties. A cationic surfactant (for example cetrimide) dissociates in aqueous solution into a cation which is responsible for the surface activity and an anion (which is generally smaller than the cation) which is devoid of surface active properties. Use of a surfactant may mean that a formulation comprising the surfactant has similar properties to that of a formulation with a higher ratio of disintegrant to sodium cromoglycate but no surfactant. Thus, an increase in the amount of surfactant used may allow the amount of disintegrant to be reduced, thus reducing the tablet size for a given amount of sodium cromoglycate. This may have the advantages that the tablet is easier to swallow, particularly for children, and will pass more easily and quickly through the empty stomach so that it arrives in the small intestine before food ingested, for example, 30 minutes later. Reduction in the amount of disintegrant, for example microcrystalline cellulose, that is required may also reduce tablet manufacturing costs.

The term "amphoteric surfactant" is well known to those skilled in the art. Such surfactants (which may also be known as ampholytic surfactants) possess at least one anionic group and at least one cationic group, and can therefore have anionic, non-ionic or cationic properties depending on the pH. If the isoelectric point of the molecule occurs at pH7, the molecule is said to be balanced. Amphoteric surfactants may have detergent and disinfectant properties. Balanced amphoteric surfactants may be particularly non-irritant, for example to the eyes and skin. The term "nonionic surfactant" is also well known in the art, for example as set out in Martindale, supra.

It will be appreciated that the composition should not contain ingredients that may cause irritation to the skin or mucosa, even on prolonged use. Compounds to which sensitisation may occur should be avoided. Thus, balanced amphoteric surfactants may be preferred.

A surfactant may be characterised on the basis of its Hydrophile-Lipophile Balance (HLB) value. The HLB scale is a numerical scale extending from 1 to approximately 50, as described, for example, in Remington supra, Chapter 21. A high HLB number (in excess of 10) indicates a hydrophilic surfactant, whilst a HLB number from 1 to 10 is considered to indicate a lipophilic surfactant.

A surfactant or combination of surfactants of any HLB value may be used. For example, a single or multiple surfactants with high HLB values may be used, a single or multiple surfactants with low HLB values may be used, or combinations of surfactants with high and low HLB values may be used. It is believed that all amphoteric or nonionic surfactants may have a beneficial effect on the dissolution of sodium cromoglycate tablets, but it is considered that an amphoteric or nonionic surfactant or surfactants with low HLB values may give the best results. Thus, amphoteric or nonionic surfactants with a low HLB value may be preferred.

By a high HLB value we mean that the HLB value is over about 10, 15, 20, 30 or 40, preferably about 10. By a low HLB value we mean that the HLB value is less than or equal to about 10, 9, 8, 7, 6, 5, 4, 3, 2, or 1.8, preferably between about 5 and 1.5. Such a surfactant may be a surfactant that is known to be useful as an antifoaming agent, water-in-oil emulsifying agent or wetting agent. Sorbitan esters, for example sorbitan fatty acid esters, are examples of surfactants with low HLB values. It is particularly preferred that the surfactant has a HLB value of less than about 2.5. An example of such a surfactant is the sorbitan ester sorbitan trioleate, which has an HLB value of 1.8. Sorbitan tristearate is a further example and has an HLB value of 2.1.

It will be appreciated that HLB values are algebraically additive, as described in Remington, supra. Thus, a blend of two surfactants with different HLB values will have a HLB value intermediate between those of the two individual surfactants. It is preferred that, if a combination of surfactants is added to the granules, the HLB value of the combined surfactants has a low HLB value, as defined above.

The HLB value for a surfactant may, if it is not already known, be determined by methods as summarised in Remington, supra, Chapter 21 and in Griffin (1949) *J Soc Cosmet Chem* 1, 311 and Griffin (1954) *J Soc Cosmet Chem* 5, 249. The ability of a compound, for example a surfactant, to spread at a surface is related to its HLB. A linear relation between HLB value and the logarithm of the dielectric constant has been observed for a number of nonionic surfactants. A HLB value may also be calculated based on the contributions of different chemical groups to the compound's HLB value (Davies 1957) *Proc Intern Congr Surface Activity*, $2^{nd}$, Butterworth, Academic, London, 426. HLB values for surfactants are given in, for example, Remington, supra and, for example in product information supplied by Croda Oleochemicals Industrial, Cowick Hall, Snaith, Goole, East Yorkshire, DN14 9AA, UK, an extract from which is shown in Table 1.

TABLE 1

Surfactants supplied by Croda Oleochemicals Industrial having an HLB value below 4.7

| HLB value | Product Name (Croda; all trade marks) | Chemical identity |
|---|---|---|
| 1.7 | Cithrol PGDO N/E | Polypropylene glycol dioleate N/E |
| 1.8 | Crill 45 | Sorbitan trioleate |
| 2.0 | Cithrol EGMS N/E | Ethylene glycol monostearate N/E |
| 2.1 | Crill 41 | Sorbitan tristearate |
| 2.4 | Cithrol PGMS N/E | Propylene glycol monostearate N/E |
| 3.2 | Cithrol PGMS S/E | Propylene glycol monostearate S/E |
| 3.3 | Cithrol GMO N/E | Glycerol monooleate N/E |
| 3.4 | Cithrol GMS N/E | Glycerol monostearate N/E |
| 3.7 | Crill 43 | Sorbitan sesquioleate |
| 3.9 | Cithrol PGMO S/E | Propylene glycol monooleate S/E |
| 3.9 | Etocas 5 | POE (5) castor oil |
| 4.0 | Crovol CR20G | POE (20%) rapeseed oil |
| 4.0 | Lanolin | Lanolin |
| 4.0 | Super Hartolan | Molecularly distilled lanolin alcohols |
| 4.3 | Crill 4 Super | Sorbitan monooleate |
| 4.3 | Crill 50 | Sorbitan monooleate |
| 4.4 | Cithrol DEGMS N/E | Diethylene glycol monostearate N/E |
| 4.4 | Cithrol GMS S/E | Glycerol monostearate S/E |
| 4.7 | Crill 3 Super | Sorbitan monostearate |
| 4.7 | Crill 6 Super | Sorbitan monoisostearate |

Examples of amphoteric surfactants include aminocarboxylic acids, aminopropionic acid derivatives, imidazoline derivatives, for example a carboxylated imidazoline derivative, dodicin, pendecamaine or long-chain betaines, Nikkol AM101® (2-alkyl-N-carboxymethyl-N-hydroxyethyl imidazolinium betaine), Nikkol AM310® (lauryldimethylaminoacetic acid betaine), Nissan Anon #300 (12 w/v % alkyldiaminoethylglycine hydrochloride, 3 w/v % alkyldiethylene-triaminoglycole hydrochloride; Inui Shouji Co, ADG), C31G (a mixture of alkyl betaines and alkyl amine oxides), N-tetradecyl-N,N-dimethyl-3-ammonio-1-propanesulfonate), cocamidopropyl betaine, disodium cocoamphodiacetate or cocoamphoacetate. Any of these may be used but it is preferred that a compound is used that has not been suggested to be linked with allergy, particularly by the oral route. Instances of allergy to cocamidopropyl betaine, when used in shampoo, have been reported (De Groot et al (1995) *Contact Dermatitis* 33(6), 419-422).

It will be appreciated that an amphoteric surfactant may be supplied (as an "amphoteric surfactant" or amphoteric surfactant preparation) packaged or compounded with other substances by the manufacturer, and that references to an amphoteric surfactant encompass an amphoteric surfactant alone and a preparation supplied as an amphoteric surfactant by the manufacturer.

A preferred amphoteric surfactant is cocamidopropyl betaine, which may be supplied, for example as a 30% aqueous solution, for example as Incronam 30 (Croda Oleochemicals, Cowick Hall, Snaith, Goole, East Yorkshire, DN14 9AA, UK).

The amphoteric surfactant may be disodium cocoamphodiacetate. It is preferred that the disodium cocoamphodiacetate is packaged or compounded with lauryl sulphate and hexylene glycol, as is known to those skilled in the art. A preferred preparation of disodium cocoamphodiacetate has the following composition:

| | |
|---|---|
| disodium cocoamphodiacetate | 14% w/w |
| sodium lauryl sulphate | 12.5% w/w |
| hexylene glycol | 7% w/w |
| sodium chloride | 3.9% w/w |
| lauryl alcohol | 1.0% w/w |
| hydrochloric acid | 1.0% w/w |
| sodium sulphate | 0.25% w/w |
| formaldehyde | 0.03% w/w |
| water | to 100% w/w |

Such a preparation may be Miracare 2MCA/E™, supplied by Rhodia Limited, Poleacre Lane, Woodely, Stockport, Cheshire SK6 1PQ.

A further preferred surfactant is an amphoteric surfactant from a coconut base, for example sodium cocoamphoacetate. This may be supplied as Miranol (Rhodia Limited, as above), in particular Miranol Ultra C32.

A preferred preparation of sodium cocoamphoacetate has the following composition:

| | |
|---|---|
| sodium cocoamphoacetate | 30-32% w:w |
| sodium glycolate | 1.8% w:w max |
| sodium chloride | 7.6% w:w max |
| sodium monochloracetate | 20 ppm max |
| colour (Gardner) | 3 max |
| solids | 38-41 w:w % |
| water | to 100 w:w % |
| pH (20% aqueous solution) | 8.5-9.5 |

A particularly preferred surfactant is sorbitan trioleate, classified as a nonionic surfactant in, for example Martindale, supra. This may be supplied as Crill 45 (Croda Oleochemicals, Cowick Hall, Snaith, Goole, East Yorkshire, DN14 9AA, UK). Sorbitan trioleate has a very low HLB value, of 1.8. Crill 45 is a liquid at room temperature. It is preferred that the surfactant is a liquid at room temperature.

The surfactant may be added to about 0.001, 0.01, 0.1, 0.5, 1, 2, 5, 10, 20, 30, 40 or 50% (w:w) of the chromone. Preferably, it is added to about 2% (w:w) of the chromone. It is preferred that the above percentages refer to the active ingredient of a surfactant formulation, for example an amphoteric surfactant formulation ie to the amphoteric surfactant component.

In particular, when the surfactant is sorbitan trioleate, for example in the form of Crill 45, the surfactant may be added to about 0.001, 0.01, 0.1, 0.5, 1, 2, 4, 5, 8, 10, 20, 30, 40 or 50% (w:w) of the chromone or granules. Preferably, it is added to between about 0.1% and 20% (w:w), still more preferably about 4% (w:w) of the granules used in preparing tablets. It is preferred that the above percentages refer to the sorbitan trioleate formulation, for example Crill 45.

For example, tablets in which the ratio of scg to microcrystalline cellulose is 1:2.5 break up satisfactorily when Crill 45 is included to 2% (w:w) of the granules. When the Crill 45 concentration is increased to 4% (w:w), the ratio of sodium cromoglycate to microcrystalline cellulose may be reduced from 1:2.5 to 1:1.5 whilst maintaining the same (satisfactory) level of tablet break-up. The tablet mass is reduced from 375 mg to 250 mg, which allows a reduction in the diameter of the tablet from 11 mm to 9 mm, which makes it much easier for patients, particularly children, to swallow. As mentioned above, the tablet will also pass easily and rapidly through an empty stomach, so that it reaches the small intestine before food swallowed, for example, 30 minutes after the tablet. The tablet manufacturing costs are also reduced as the quantity of microcrystalline cellulose that is required is reduced.

A further aspect of the invention is therefore an oral drug delivery composition comprising a chromone, wherein the composition further comprises (1) an amphoteric surfactant, for example cocamidopropyl betaine or sodium cocoamphoacetate, and/or (2) a surfactant having a HLB value of less than 2 or being a sorbitan ester having an HLB value of less than 10, preferably less than 5, for example a sorbitan fatty acid ester, for example sorbitan tristearate. Preferably, the chromone is made bioavailable in the small intestine following human oral administration, and still more preferably is made bioavailable within 10 minutes of exposure of the composition to simulated intestinal fluid, and/or has the other preferred properties indicated above.

A further aspect of the invention is the use of an amphoteric surfactant or a surfactant having a HLB value of less than 2 or being a sorbitan ester having an HLV value of less than 10, preferably less than 5, for example a sorbitan fatty acid ester, for example sorbitan tristearate, in the manufacture of a medicament for treating a patient with an allergic condition wherein the medicament is administered orally. It is preferred that the medicament comprises sodium cromoglycate.

In a less preferred granulation method, granules can be prepared by coating non-pareil seeds with the sodium cromoglycate or by forming a core comprising sodium cromoglycate dispersed therein. Suitable binding agents which may be used in forming such a core are known in the art. The excipients used to prepare the seeds may comprise one or more of pharmaceutically acceptable materials, eg sugar, starch, microcrystalline cellulose, waxes and polymeric binding agents, such as those listed below. The first layer on the non-pareil seeds may comprise the sodium cromoglycate and a water-soluble or water-insoluble polymer which acts both as binder for the sodium cromoglycate and as a rate-limiting layer for release of the sodium cromoglycate. Such polymers may be selected from cellulose derivatives, vinyl polymers and other high molecular polymer derivatives or synthetic polymers such as methylcellulose, hydroxypropylcellulose, hydroxypropylmethylcellulose, ethylcellulose, cellulose acetate, polyvinyl pyrrolidone, polyvidone acetate, polyvinyl acetate, acrylic polymers and copolymers, polymethacrylates and ethylene-vinyl acetate copolymer or a combination thereof. Preferred film-forming polymers are ethylcellulose or copolymers of acrylic and methacrylic acid esters (Eudragit NE, Eudragit RL, Eudragit RS) in aqueous dispersion form.

The optionally first rate-limiting layer on the seeds with homogeneously distributed sodium cromoglycate may comprise a water insoluble polymer or a mixture of water insoluble polymers or a mixture of water soluble and water insoluble polymers mentioned above. It will be appreciated that it is preferred that any such rate-limiting layer does not prevent the sodium cromoglycate from being released from the formulation within 10 (or less; as set out above) minutes of the formulation being exposed to intestinal fluid or simulated intestinal fluid.

The coatings may optionally comprise other pharmaceutically acceptable materials which improve the properties of the film-forming polymers such as plasticizers, anti-adhesives, surfactants, and diffusion-accelerating or diffusion-retarding substances. Suitable plasticizers comprise phthalic acid esters, triacetin, dibutylsebacate, monoglycerides, citric acid esters and polyethyleneglycols. Preferred plasticizers are acetyltributyl citrate and triethyl citrate. Suitable anti-adhesives comprise talc and metal stearates.

The amount of the first coating (if used) applied on the units may be in the range between 0.5% and 30% by weight, preferably between 1% and 15%. This amount includes in the relevant case the weight of the sodium cromoglycate as well. The amount of coating (which may be one or two coatings) applied on the units may be in the range between 1 and 50% or 5% and 60% by weight, preferably between 5% and 50% or 2% to 25%, calculated on the weight of the coated units. The remainder constitutes the weight of the seed or core. It is thus clear that the above percentages refer to the coating as a percentage of the final weight of the units after coating. Alternatively, the amount of the coating may be in the range between 5 and 120%, preferably between 5 and 100%, more preferably between 5 and 50%, most preferably between 6 and 10% by weight of the weight of the seed or core or active ingredient.

For example, in one process, sodium cromoglycate powder (in which 90% of the particles may have a diameter of less than 30 μm) is spray granulated in a fluid bed dryer in combination with water and HPMC to agglomerate the particles into larger particles.

Alternatively, the sodium cromoglycate can be mixed with a melt binder such as polyethylene glycol, heated to its melting point in a high shear mixer and cooled, as discussed in Example 3. This produces rather larger particles of about 200 μm, or 200 to 1100 μm.

The granules/particles may then be formed into a tablet (or alternatively packaged in a capsule) with a disintegrant in the ratios described, and the tablet (or capsule) enteric coated. Alternatively, the sodium cromoglycate may be granulated with the disintegrant and/or surfactant in the ratios described and the granules enteric coated and/or formed into a tablet or packaged in a capsule which is then enteric coated.

It is preferred, particularly when a surfactant is to be incorporated in the granules, that the granules are produced using a fluid bed system using top spray or bottom spray (co-current or counter-current) methods and then enteric coated using an apparatus in which unacceptable levels of damage to the granules can be avoided. Such an apparatus may be a tablet coater as described, for example, in Aeromatic Fielder's patent application DK9900116, which describes an apparatus in which partitions present in other apparatus are omitted. This has the effect of reducing damage to the granules or tablets being coated. The apparatus muffles the atomizing gas after leaving the nozzle to decrease upward scattering of the tablets.

A tablet in which the core has the above ratio of disintegrant to chromone may further be coated in disintegrant prior to any enteric coating. It is preferred that such a coating of disintegrant substantially does not comprise a chromone.

The composition may comprise more than one disintegrant. For example, the disintegrant(s) mixed with the chromone and that/those used as a further coat around the chromone-containing core may be different.

It is preferred that the disintegrant does not comprise heavy metal or alkaline earth ions as a significant constituent (ie more than about 10, 20, 30 or 40% w:w). Di-calcium phosphate, for example, comprises $Ca^{2+}$ ions and may therefore not be suitable.

The composition may further comprise other compounds, for example bulking agents and/or lubricants and/or a surfactant and/or an enteric coating. However, it preferred that the composition consists substantially of the chromone (which may comprise water), disintegrant, a lubricant, for example magnesium stearate, a surfactant, for example Miranol or sorbitan trioleate, and an enteric coating. It is preferred that ingredients selected from this list form in combination at least 70%, 80%, 90%, 95% or 98% of the composition. It is preferred that the chromone (which may comprise water) and disintegrant together form at least 40%, 50%, 70%, 80%, 85% 90%, 95% or 98% of the composition. The enteric coating may typically form between about 30% and 2% of the mass of the tablet, preferably between about 20% and 3%, still more preferably between about 15% and 5%, for example about 10% of the mass of the tablet.

It is preferred that the composition does not comprise an allergen, particularly an allergen to which the prospective patient is thought to be allergic. However, a composition of the invention comprising such an allergen may be of use in desensitisation treatment, for example as described in WO85/00015.

It is also preferred that the composition does not comprise a physiologically acceptable, pH-regulating alkaline material in an amount sufficient to produce a significant pH change when released in the small intestine. The pH-regulating alkaline material is substantially insoluble (ie 10,000 and over parts of solvent required for 1 part of solute) in intestinal fluid exhibiting a neutral or alkaline pH. It may be an acid soluble salt. It may be a substantially insoluble carbonate, bicarbonate, silicate, hydroxide or phopshate, preferably of an alkaline earth metal, more preferably magnesium or calcium, for example calcium carbonate.

In a further embodiment of the first aspect of the invention, the composition comprises pellets of between 0.7 and 5 mm diameter, comprising the chromone, wherein each pellet is substantially spherical and has an enteric coating.

A further aspect of the invention is an oral drug delivery composition comprising a chromone, wherein the composition comprises substantially spherical pellets of up to 5 mm diameter comprising the chromone, each pellet having an enteric coating. The pellets may further comprise a surfactant, for example an amphoteric surfactant or a surfactant having an HLB value of less than about (in order of preference) 2, 3, 4, 5, 6 or 6.8, or being a sorbitan ester, for example a sorbitan fatty acid ester, for example sorbitan trioleate, as described above and further below. Preferably, the chromone is made bioavailable in the small intestine following human oral administration.

We have found that enteric coating of pellets that are not substantially spherical may not be effective. Although the pellets may appear to have been coated, we have found that the coating may disintegrate at a different pH from that intended. For example, a coating expected to disintegrate at a pH of about 5 or more may disintegrate at a pH of about 3.5.

By "substantially spherical" is meant that the pellet has the appearance of a sphere when examined by the unaided eye. It is preferred that the uncoated pellet is also substantially spherical in order to provide a substantially spherical pellet after it is coated.

It is preferred that the pellets have a diameter of between 0.7 mm and 5 mm, 4 mm, 3 mm, 2 mm, 1.8 mm, 1.5 mm or 1.3 mm, preferably between 0.8 and 1.5 mm. These dimensions refer to the enteric coated pellet. The uncoated pellets may have dimensions between 0.5 mm and 4.8 mm, 3.8 mm, 1.8 mm, 1.6 mm, 1.3 mm or 1.1 mm, preferably between 0.6 mm and 1.3 mm. These figures preferably refer to at least 50%, preferably at least 75%, 90%, 95%, 99% and most preferably 100% of the pellets in the composition (by number).

Substantially spherical pellets comprising a chromone may be prepared, for example, by mixing with a melt binder such as polyethylene glycol, heating to its melting point in a high shear mixer and cooling. The pellets are then dried in a fluid bed drier. The pellets may be referred to as melt pellets. An example of such a method of preparing the pellets is given in Example 2.

The melt binder may be an aqueous binder described above. Examples include polyethylene glycol (PEG), polyvinylpyrrolidone (PVP) and hydroxypropylmethylcellulose (HPMC). PEG may be preferred as it may give a strong granule that is particularly suitable for coating.

As described above for the preparation of granules for formulation with a disintegrant, a surfactant, preferably an amphoteric surfactant or a surfactant having an HLB value of less than about 2, 3, 4, 5, 6 or 6.8, for example sorbitan trioleate, may be added to the chromone, for example with the binder. Preferences for the surfactant and the quantities that may be used are as described above.

The pellets or tablets or capsules may be enteric coated using a fluid bed based coating system or using the coating pan technique in a side vented pan, as well known to those skilled in the art. A tablet coater as described in DK99/00116 may be used, as described above.

It is preferred that the pellets are enteric coated such that the chromone is made bioavailable in the duodenum, as described above.

The polymers used to enteric coat a tablet, capsule or pellet may be selected from the group of anionic carboxylic polymers suitable for pharmaceutical purposes and being soluble only with difficulty at a low pH but being soluble at a higher pH, the pH limit for solubility being in the interval of pH 4 to pH 7.5, said group comprising cellulose acetate phthalate (for example Aquateric; FMC Corporation, Pharmaceutical Division, 1735 Market Street, Philadelphia, Pa. 19103), cellulose acetate trimellitate, hydroxypropylmethylcellulose phthalate, polyvinyl acetate phthalate and acrylic acid polymers eg partly esterified methacrylic acid polymers such as Eudragit L, Eudragit L100-55 and Eudragit S. These polymers may be used alone or in combination with each other or in combination with water insoluble polymers mentioned before. Preferred polymers are the Eudragits in aqueous dispersion form. The anionic carboxylic polymer may comprise 25 to 100% of the total polymer content.

The enteric coatings may optionally comprise other pharmaceutically acceptable materials which improve the properties of the film-forming polymers such as plasticizers, anti-adhesives, surfactants, and diffusion-accelerating or diffusion-retarding substances. Suitable plasticizers comprise phthalic acid esters, triacetin, dibutylsebacate, monoglycerides, citric acid esters and polyethyleneglycols. Preferred plasticizers are acetyltributyl citrate and triethyl citrate. Suitable antiadhesives comprise talc and metal stearates.

The amount of the enteric coating applied on the units is normally in the range between 1% and 50% by weight, preferably between 2% and 25%, still more preferably between 10-15%, most preferably about 12%, calculated on the weight of the coated units.

The capsule may be a gelatin capsule (for example, a capsule which consists essentially of gelatin) which may then enteric coated as described above. Suitable capsules are well known to those skilled in the art. The capsules should not be such that they may pass through the small intestine or even the whole gastrointestinal tract substantially intact. The capsules may be such that if they were used without the enteric coating they may release their contents in the stomach.

It is preferred that the enteric coating is chosen such that maximum disintegration of the coated capsules occurs within the small intestine (duodenum, jejunum, ileum), preferably within the duodenum. Preferably, substantially all of the administered chromone is made bioavailable from the duodenum onwards.

It is preferred that the tablet (or capsule) is able to pass through the stomach and into the small intestine (ie through the pylorus). Thus, it is preferred that the tablet may have a final weight of up to 500 mg for use in children, preferably between 200 and 500 mg, still more preferably between 220 and 375 mg. A larger tablet may be acceptable in adults. It is preferred that the tablet size is such that the tablet may be swallowed easily by a child (for example, has dimensions less than about 0.8 or 0.9 cm). It is preferred that each tablet contains less than an intended daily dose of sodium cromoglycate, so that more than one tablet may be taken per day, as discussed below.

If the tablet or capsule is not enteric coated and comprises pellets that are enteric coated then it is expected that the tablet or capsule will disintegrate in the stomach and release the enteric coated pellets into the stomach contents. Enteric coated pellets may therefore become mixed with the stomach contents and enter the duodenum with portions of the stomach contents. Once exposed to intestinal fluid in the duodenum, the enteric coat of each pellet may disintegrate, releasing pellets of sodium cromoglycate which may have a sufficiently large surface area:mass ratio that the sodium cromoglycate may enter solution.

It is preferred that the chromone is made bioavailable in the duodenum, as described above. However, although less preferred, it may be beneficial if differing groups or populations of the individual pellets (for example) have differing enteric coatings such that the drug content of the pellets is first made bioavailable at differing locations in the small intestine.

Two particular ways in which the drug can be made bioavailable at differing times, and therefore differing locations of the small intestine as the contents pass through the intestine, are to coat the pellets/tablets/capsules with differing thicknesses of the same enteric coating or to use differing enteric coating materials which dissolve at differing pH's. This may provide a non-pareil formulation. Both formulations take advantage of the fact that the pH of the contents of the intestine gradually rises as the contents pass from the stomach into and through the small intestine. Suitable enteric coatings are known in the art and are discussed in more detail below.

The enteric-coated pellets can be filled into capsules, compressed into tablets or filled into unit-dose sachets, the contents of which may be suspended in a liquid at a suitable pH immediately prior to use and drunk by the patient. Thus, the enteric-coated pellets may be taken orally as a suspension in a liquid (for example reconstituted as a suspension in a liquid at the time of use), preferably with food, or they may be packaged in tablets or capsules, for example of gelatin, which make the preparation easy to swallow but which disintegrate in the stomach, thus helping to mix the pellets evenly with food.

The composition of the coating should be optimised to maximise disintegration of the coating within the small intestine (duodenum, jejunum, ileum), preferably the duodenum, and to minimise the possibility of the coated microgranules/pellets passing through the small intestine, or even the whole gastrointestinal tract, intact. Preferably, drug is made bioavailable from the duodenum onwards.

Any coating can be used which ensures that the microgranules or capsules do not break up and release the drug until they are in the small intestine. The coating may be one which is pH-sensitive, redox-sensitive or sensitive to particular enzymes or bacteria, such that the coating only dissolves or finishes dissolving in the small intestine. Thus, the microgranules or capsules will not release the drug until they are in the small intestine.

The amount of the coating will typically be in the range of 4-20% w/w on dry granules, or 5 to 120% w/w of the weight of the dry granules before the coating is applied. The amount of the particular coating used will be chosen according to the mechanism by which the coating is dissolved. Suitable amounts of coating for a capsule are well known to those skilled in the art.

Preferred coating materials are those which dissolve at a pH of 5 or above, for example pH 5.5 to 7.5, such as polyacids having a $pK_a$ of 3 to 5. The coatings therefore only begin to dissolve when they have left the stomach and entered the small intestine. Such a coating can be made from a variety of polymers such as cellulose acetate trimellitate (CAT), hydroxypropylmethyl cellulose phthalate (HPMCP), polyvinyl acetate phthalate (PVAP), cellulose acetate phthalate (CAP), hydroxypropyl methylcellulose acetate succinate (HPMCAS), carboxymethyl ethylcellulose (CMEC) and shellac as described by Healy in his article "Enteric Coatings and Delayed Release" Chapter 7 in "Drug Delivery to the Gastrointestinal Tract", editors Hardy et al, Ellis Horwood, Chichester, 1989, or in Chapter 93 of Remington's: "The Science and Practice of Pharmacy", 19th Edition. PVAP is preferred to CAP or CAT, as it dissolves at a lower pH and hence ensures bioavailability from the duodenum onwards.

Other materials include methylmethacrylates or copolymers of methacrylic acid and methylmethacrylate. Such materials are available as Eudragit polymers (trademark) (Röhm Pharma, Darmstadt, Germany). Eudragits L, S, "L and S" and LD are anionic copolymers of methacrylic acid and methylmethacrylate and are generally suitable. For example Eudragit L100 (50% free carboxyl groups) or S100 (30% free carboxy groups) may be used. Eudragit L100-55 is especially suitable and is obtained from L30 D-55 by spray-drying. It has equal amounts of methacrylic acid and ethyl acrylate and about 50% free carboxyl groups.

The pellets can also be given a sustained or controlled release property, should this be considered desirable, for example with waxes or silicone elastomers, especially by using melt granulation techniques.

A chelator of heavy metal ions, such as EDTA, can be included in a formulation of any aspect of the invention in order to prevent insoluble heavy metal ion salts or complexes of cromoglycate being formed. To be most effective, the chelating agent should be included in the granules or pellets but, alternatively, it can be mixed with the granules or pellets.

Suitable dosage regimes include the following. An initial daily dose of 1 mg to 2 g, preferably 100-1000 mg, more preferably about 200-800 mg, still more preferably about 300 to 500 mg is given in, for example, two divided doses spaced 12 hours apart. This may be increased at intervals of, say, 1-3 weeks, to a maximum of 1000-5000 mg daily. A typical maximum daily dose is 4000 mg or 100 mg/kg/day (whichever is the greater).

It is preferred that the daily dose is administered in the form of multiple tablets or capsules. For example, the daily dose may be administered as one tablet taken four times a day or as two tablets taken four times a day ie as eight tablets. This may have the benefit that sodium cromoglycate solution is released in the small intestine four or eight times during the day, respectively. It is preferred that the composition is administered before food, for example about 30 minutes before a meal, preferably when the patient has a substantially empty stomach, ie at least two hours after the previous meal.

A further aspect of the invention provides a method of treating a patient for an allergic condition by orally administering a composition of the invention. The patient may first have been tested for serum IgE level and have been found to have a total level of at least 150 iu/ml.

Suitable IgE tests include an in vitro total IgE test and an in vitro specific IgE test, for example the UniCAP Total (or Specific) IgE tests sold by Pharmacia & Upjohn, which use the Allergen ImmunoCAPs as the allergen reagent.

We have found that it is desirable for patients to be screened according to their IgE levels before treatment with sodium cromoglycate is undertaken. More specifically, we believe that patients with total serum IgE levels below 150 iu/ml are less likely to respond to the treatment. Although previous trials have measured IgE levels, the patients have not been selected for treatment according to the IgE level. This is one reason why we believe that the prior art studies have created the impression that sodium cromoglycate is not always effective in treating these allergic conditions.

Hence, according to a further aspect of the invention, a patient is selected for therapy according to whether their total serum IgE level is above 150 iu/ml. They may be tested immediately before therapy, or reference may be made to earlier test results.

The pathophysiology of food allergy and food allergic disease is unknown but we consider that the primary defect in a number of patients is an allergic inflammatory reaction in the mucosa of small intestine, in particular the jejunum, caused by a reaction between specific substances in the food and specific IgE antibodies to that food produced by the patient. This allergic inflammatory reaction may cause symptoms itself but commonly does not. We consider that it results in an alteration in gut permeability allowing increased absorption of a number of substances, including those substances to which the patient is allergic. It is the increased absorption of these substances which causes secondary allergic reactions in secondary target organs, such as the skin in the case of atopic dermatitis and urticaria, the bronchial mucosa in the case of asthma, the nasal mucosa in the case of rhinitis and the colonic mucosa in the case of irritable bowel syndrome.

We further consider that the primary mode of action of orally administered sodium cromoglycate in the treatment of food allergy is to reduce the severity of the IgE-mediated allergic inflammatory reaction in the mucosa of the small intestine and therefore prevent the increased absorption of allergic substances. As the severity of the allergic reaction in the secondary target organs is related to the amount of allergen reaching the organ, this effect of the drug will be to reduce the severity of the allergic reaction in the secondary target organ.

It has recently been shown that an additional effect of sodium cromoglycate is to reduce the ability of IgE-producing cells, the B lymphocytes, to synthesise IgE antibody. It is proposed that the relevant B lymphocytes in the case of food allergy are found in the mucosa of the small intestine.

The present invention therefore provides a long-term treatment with oral sodium cromoglycate, based not only on its ability to reduce the consequences of the acute antigen/IgE antibody reaction but also the overall sensitivity by reducing the local synthesis of IgE antibody. This will initially be seen in the reduction in locally measured IgE antibody and ultimately in the amount of IgE antibody measured systemically, that is in the blood as Total Serum IgE.

The basis of an aspect of this invention is that the efficacy of oral sodium cromoglycate in the treatment of food allergic conditions will be increased by selecting patients who have clear evidence of an IgE mediated disease and whose clinical response is associated with a reduction in initially local and subsequently systemic levels of IgE antibody and secondly by increasing the bioavailability of the drug with a formulation that maximises the concentration of the drug in the secretions of the small intestine, in particular throughout the length of the jejunum.

Preferred aspects of the invention will now be described by way of reference to the following non-limiting examples.

EXAMPLE 1

Granule Formation (1)

The following solutions are made up:

| Formulation A1, A2 or A3: | | |
|---|---|---|
| Formulation A1: | | |
| Water (purified) | 1000 g | |
| Sodium Cromoglycate | 150 g | solids 14.29% |
| Hydroxypropyl methyl cellulose | 16.68 g | |
| | 1166.7 g | |
| Formulation A2: (for a larger and stronger granule) | | |
| Water (purified) | 2000 g | |
| Sodium Cromoglycate | 300 g | |
| Hydroxypropyl methyl cellulose | 54 g | |
| | 2354 g | |
| Formulation A3: (for an even stronger granule) | | |
| Water (purified) | 2000 g | |
| Hydroxypropylmethyl cellulose | 222 g | |
| | 2222 g | |

A coat of solids constituting 12% of the mass of the granules (12% (solids) coat) on 1000 g of granule requires 1065 g of a suspension having 11.27% solids.

1000 g of powder Sodium Cromoglycate is placed into the bowl of an MPI Spray Granulator (Aeromatic-Fielder-UK) and fluidised using hot air at an inlet temperature of 70° C. The air rate used is approx 100 m³/hr.

Once the material is fluidised and the powder bed has reached a temperature of 40° C., Formulation A1, A2 or A3 is sprayed through a two fluid nozzle placed above the fluidised bed, using atomizing air at approx 2 bar, to produce granules. The rate used is approx 27 g/min and therefore the time taken to spray 1167 g of solution is approx 44 minutes.

Once spraying has been completed the product is allowed to dry in the hot air stream until the bed temperature reaches 46° C. (The lowest bed temp reached is 35° C.)

If all the powder is collected, then the weight yield should be 1000+the solution solids=1166.7 g.

However, the typical yields obtained were around 90%.

The granules may then be formed into tablets with a disintegrant.

EXAMPLE 2

Granule Formation (2)

Granulation is desirable in order to improve flow and compression characteristics when preparing a dosage form, such as a tablet or capsule.

Wet Granulation

Spray granulation in a fluid bed system is used to produce free flowing sodium cromoglycate granules:

Sodium cromoglycate is fluidised in the fluid bed with a diluent to aid fluidisation, for example microcrystalline cellulose. Onto the powder bed is sprayed a solution of binder and/or surfactant such as the amphoteric surfactant Miranol Ultra C32 or sorbitan trioleate. The binder may be sodium cromoglycate, PVP, HPMC, PEG or other water soluble binder.

Water may be used without additional binder or surfactant. This is because of the limited solubility of the sodium cromoglycate (freely soluble up to 5% and soluble with difficulty up to 10%).

A chelating agent such as EDTA at 0.1% may be included.

The strength and size of the granules may be changed by varying the binder quantity and type. The binder may typically be used at about 10% (w:v) of the sodium cromoglycate.

The granule is dried in the same equipment, producing a free flowing material.

For a 500 g batch size, typical conditions may be:

Inlet air temperature: 70° C.

Bed temperature: 30° C. to 40° C., typically 30° C. to 35° C.

Spray rate: 20-25 g/minute

Air rate in fluid bed: 70-100 cubic meters/hour

Spray binder solutions typically have a solids contents w:w of 10-15%.

These conditions may require adjustment with changes in batch size.

The particle size of granules produced can be varied from 100 μm up to about 750 μm. A suitable median particle size is about 200 μM.

Drying: the end point for drying may be assessed by measuring the temperature of the bed—as the granules become drier, the temperature of the bed rises. An end point bed temperature of 45-50° C. gives a Loss on Drying (LOD) of 4.0-8.0%. LOD means the mass loss recorded after 20 minutes at 105° C. in an infrared balance system. The granule can be run drier by setting the end point as 50-55° C. bed temperature.

Dry Granulation

Sodium cromoglycate may be granulated by roller compaction and the resulting granules put through a reducing mill and sized, as known to those in the art.

Wet or dry-formed granules produced as above (or granules produced as described in Example 1) are then combined with a disintegrant, for example microcrystalline cellulose and a suitable lubricant such as magnesium stearate to produce a compression mix which is subsequently tabletted.

A ratio of at least 2.5 parts microcrystalline cellulose to 1 part sodium cromoglycate granules may be required for fast tablet disintegration, for example 250 mg microcrystalline cellulose to 100 mg sodium cromoglycate granules. If a surfactant is included in the granules, then a lower ratio, for example 1.5 parts microcrystalline cellulose to 1 part sodium cromoglycate granules may be sufficient.

Tablets may typically contain 261 mg microcrystalline cellulose (for example, Avicel PH101 or Avicel PH102). The final tablet weight for 100 mg active is 375 mg. This may be tabletted on an 11 mm double radius normal concave tablet punch and punched to a hardness of between 4 and 10 kilograms (the term used in the art, which may correspond to kilograms per $cm^2$).

The tablet may be enteric coated using a fluid bed based coating system or using the coating pan technique in a side vented pan. Shuteric (polyvinyl acetate phthalate, Colorcon Ltd, Orpington, UK) or Eudragit, Aquacoat, Aqoat or Aquateric may be used as the enteric coating. The tablets are coated to a level of 5 to 20%, usually 10 to 15%, particularly 12%.

Filling into Capsules

Alternatively, an appropriate fill of sodium cromoglycate and disintegrant, for example 100 or 200 mg sodium cromoglycate per capsule, is weighed into hard gelatin capsules, and the capsules sealed and enteric coated in a fluidised spray coater or rotary coating pan. The fill may comprise granules comprising sodium cromoglycate and disintegrant, for example microcrystalline cellulose and optionally a surfactant, for example an amphoteric surfactant, such as Miranol Ultra C32. The ratio of disintegrant to sodium cromoglycate in the granules may be more than 1.2:1 :w:w, preferably between about 1.4:1 and 2.5:1.

EXAMPLE 3

Granulation—High Shear Mixer Method

An alternative method involves the use of high shear mixer technology using a melt granulation technique.

Stage one—this process involves mixing SCG with a melt binder such as PEG under ambient conditions. The mixture is then heated to the melt point of the binder (approx 60° C.) in a high shear mixer and mixed intensely to produce a round particle of approximate size 200 to 500 μm, and then cooled.

Stage two—these particles are then enteric-coated in a fluid bed spray coater (obtainable from Aeromatic-Fielder Ltd, Hampshire, UK) with AQOAT (Shin-Etsu), Aquateric (cellulose acetate phthalate aqueous redispersible powder and a suitable plasticizer, for example diethyl phthalate (DEP); FMC Corporation, Pharmaceutical Division, 1735 Market Street, Philadelphia, Pa. 19103) or one of the other commercially available coatings such as a CAP (FMC), CAT (Eastman Kodak), PVAP (Colorcon), or a Eudragit (Röhm Pharma).

Enteric Coating the Individual Granules 1000 g of the above produced granules are now transferred to the bowl of a fluid bed coater such as an MPI Precision Coater, which uses an upspray system for spraying a coating solution/suspension on to the fluidised granules.

The atomizing air pressure is approx 3 bar.

The bed of granules is preheated to a temperature of approx 36° C. (inlet air temperature of 60° C. used) before spraying commences.

The coating solution (Formulation B) is sprayed onto the granules at an approx rate of 18 g/min using atomizing air pressure of approx 3 bar and therefore the time taken to spray 1065 g of solution is approx 60 mins (1 hour). During the coating the temperature of the granules gradually drops and by the end has reached approx 25° C. Once all the coat has been added the bed is allowed to heat up to approx 40° C. before stopping the process to allow the coat to dry. Total process time including drying is approx 1½ hours (90 mins). In nearly all cases/batches produced to date the yields have been very good at 100%.

Coating Suspension

| Formulation B: | % | | for 1000 g of granule |
|---|---|---|---|
| Aqoat HPMC-AS-LF | 7.0 | | 74.55 |
| Triethyl Citrate | 1.96 | | 20.87 |
| Talcum Powder | 1.1 | solids: | 11.72 |
| Titanium Dioxide | 1.0 | 11.27% | 10.65 |
| Sodium Lauryl Sulphate | 0.21 | | 2.24 |
| Purified Water | 88.73 | | 944.97 |
| | 100.00 | | 1065 g |

Finally, the coated granules are filled into capsules for the final dosage form.

Stage three—these coated particles may then be used to produce a variety of oral dosage forms such as capsules to be swallowed, or tablets to be swallowed, or filled into unit-dose sachets the contents of which may be suspended in a liquid of suitable pH immediately prior to use and drunk, or partially filled into bottles to which a suitable diluent is added, by the pharmacist immediately prior to it being dispensed, and drunk.

EXAMPLE 4

Patients with symptoms of food allergy or chronic disease such as irritable bowel syndrome, rhinitis, asthma, conjunctivitis, atopic dermatitis, urticaria, migraine, eczema or hyperactivity in which allergy to foods has been shown to be a causative factor are investigated for total serum IgE levels by the Pharmacia & Upjohn UniCAP Total IgE Test, and preferably also investigated for sensitivity to food or drink by the Pharmacia & Upjohn UniCAP Specific IgE Test and/or skin prick tests to ingested allergens. If total serum IgE levels are above 150 iu/ml or if a skin prick test or UniCAP Specific IgE test is positive the patient should be considered for treatment with the formulation of the invention.

Adults and children over 12 years of age should be started on a daily dose of from 400 mg a day taken before food in two divided doses, for example at 8.00 am and 8.00 pm. Capsules or tablets should be swallowed whole with water, not milk, milkshake, fruit juice or other potentially allergic foodstuff.

Children between the ages of 12 and 5 years should be started on a daily dose of from 200 mg a day taken before food in two divided doses, for example at 8.00 am and 8.00 pm. Capsules should be swallowed as above.

Children below 5 years of age should be started on a daily dose of from 50 to 100 mg a day taken before food in two divided doses, for example at 8.00 am and 8.00 pm. Capsules should be swallowed as above.

Patients may initially experience a worsening of symptoms. This is a positive sign that the medication is having an effect. In these patients the dosage should be reduced to half for 1 week before being increased again. Alternatively an anticholinergic drug such as dicyclomine hydrochloride or propantheline bromide may be administered concurrently for the first week.

After 4 weeks another serum IgE measurement should be taken. If this is lower it may indicate that the patient is responding even if there is no symptomatic improvement.

Serum IgE measurements should continue to be taken at monthly intervals for 6 months, 3 monthly for a further 6 months and 6 monthly thereafter. A maintained reduction in levels will indicate a reduction in sensitivity to the ingested allergens and symptomatic improvement in the condition.

It is important that patients continue to take their medication even though their symptoms are absent or significantly improved. If they do not, their IgE levels will begin to increase again and when they start the medication again it will take time for the IgE levels and therefore the symptoms to subside—but patients will not wait and will conclude that the medication is ineffective.

EXAMPLE 5

Factors Affecting the Clinical Efficacy of Sodium Cromoglycate

Sodium cromoglycate may have a bell-shaped dose response curve or S-shaped dose response curve. In either case it means that if a sufficient concentration of drug is not present the desired clinical effect may not be achieved.

The following model of gut fluid dynamics may be used in calculating concentrations of sodium cromoglycate achieved in the small intestine.

References which discuss gut properties and fluid dynamics are indicated below.

The following assumptions are made:

The drug is water soluble, poorly absorbed (1-2%), not adsorbed to food particles or gastric mucosa, acid insoluble (pKA 2), lipid insoluble.

In a day, the average stomach passes 8 liters (6 mls/min) and the average volume of fluid contained in the stomach is 100 mls.

If, for example, a patient is pre-dosed with sodium cromoglycate and then, 15 minutes later, challenged with food (approximately 90 ml volume), then the total volume diluting the sodium cromoglycate during that time is 100 ml (stomach contents)+90 ml (meal volume)=190

The concentration of sodium cromoglycate leaving the stomach may be (dose (g)×100/190 ml)% (w:v).

Therefore, if the dose is 800 mg, the concentration is 0.42%, for 400 mg, 0.21%, for 200 mg, 0.11%, and for 100 mg, 0.5%.

However, this concentration of sodium cromoglycate is very unlikely to be bioavailable if it has been exposed to gastric fluid as it is insoluble in an acid medium and will not dissolve even on entering a less acid medium, as discussed above.

Nalcrom™ is presented as a capsule from which a drink is prepared by pulling the capsule apart and dissolving the contents in hot water, followed by dilution with cold water. Alternatively, Nalcron™ (France) and Lomudal Gastrointestinal™ (Scandinavia) are presented as 2% solution in an ampoule, the contents of which are drunk.

For a Nalcrom™ dose, the concentration of the solution as drunk is 0.2 g in 50 ml ie 0.4%.(w:v). The concentration (probably not in solution) in the stomach after dosing may be 0.13% (0.2 g/150 ml).

After 4 hours, 1300 ml of fluid may have passed through the stomach, so the concentration in the stomach (probably not in solution) at this time may be 0.2 g/1300 ml ie 0.015% (w:v).

Concentration of Sodium Cromoglycate Achieved by Gastrofrenal™ in the Stomach.

Gastrofrenal™ is presented as a powder of sodium cromoglycate mixed with 5 g of sugar in a sachet. The contents of the sachet are poured into a glass, water added and the solution/suspension drunk.

500 mg is delivered in 140 ml to the stomach, so the initial concentration may be 0.5 g/240 ml ie 0.2%.

Altolyn™—a Formulation of the Invention Comprising Disintegrant.

Altolyn™ is a tablet formulation which may release, for example, 100 mg of sodium cromoglycate in a rapid burst early in the small intestine.

If an aliquot of 150 ml travels through the pyloric sphincter with a tablet containing 100 mg sodium cromoglycate, this provides 0.1 g/150 ml ie 0.067% (w:v). For a tablet containing 200 mg sodium cromoglycate, this provided 0.2 g/150 ml ie 0.13% (w:v). If an aliquot of 15 ml or 5 ml travels through the pyloric sphincter with a tablet containing 100 mg sodium cromoglycate, the concentration would be 0.1 g/15 or 0.1 g/5 ml ie 0.67% (w:v) or 2% (w:v).

If an aliquot of 111 ml travels through the pyloric sphincter (8 liters/24 hr=111 ml/20 min), then the concentrations achieved will be 0.09% and 0.18% (w:v) respectively.

The burst is triggered by the enteric coating on the tablet dissolving rapidly as soon as it reaches alkaline conditions. The liquid then reaches the inner core of the tablet and causes the disintegrant combined with the sodium cromoglycate to swell and disperse the active ingredient very quickly.

The tablet may also contain a chelating agent to ensure the maximum is dose of cromoglycate is maintained as the sodium salt (ie is not precipitated out as an insoluble salt).

The preferred dosage of the formulation may be 2 tablets eight times a day, so that a burst of sodium cromoglycate is released in the small intestine 8 time during the day.

The use of a disintegrant in an enteric coated tablet formulation may assist the sodium cromoglycate in dispersing rapidly in the small intestine. Formulation of sodium cromoglycate is difficult because the physical properties of sodium cromoglycate are unusual. In other tablet formulations of sodium cromoglycate, the sodium cromoglycate immediately forms a glutinous gel which seals the drug preventing further wetting.

EXAMPLE 6

Tablets Incorporating Sorbitan Trioleate

Tablets are prepared from sodium cromoglycate granules comprising sorbitan trioleate. The sorbitan trioleate is supplied as Crill 45 by Croda Oleochemicals—Healthcare, Cowick Hall, Snaith, Goole, East Yorkshire, DN14 9AA, UK.

Tablets made up of sodium cromoglycate granules (which may include 2% Crill 45 (w:w)) and microcrystalline cellulose in the ratio of 1 (sodium cromoglycate granules):2.5 (microcrystalline cellulose) break up satisfactorily (ie in less than 10 minutes) when exposed to water. When the Crill 45 content of the granules is increased to 4%, the ratio of granules to microcrystalline cellulose can be reduced from 1:2.5 to 1:1.5 whilst still achieving consistently satisfactory (ie in less than 10 minutes) break-up on exposure to water.

Based on in vitro measurements, the sodium cromoglycate is released early in the small intestine. The tablets are able to produce an effective concentration of sodium cromoglycate in the small intestine, as shown, for example, by the results of the trials indicated below.

The observed clinical effect is much greater than that achieved using the current commercially available formulation of sodium cromoglycate (Nalcrom™). This improved clinical effect is evident in either a challenge situation or in chronic dosing for the management of allergic diseases of the small intestine, as shown by the following examples.

Male AE, aged 59, with a history of sensitivity to onions. Three tablets (3×100 mg) were taken with water half an hour before ingesting onions. The usual reaction of diarrhoea and griping pains were completely blocked.

Male AW aged 46, life-long vegetarian with a history of allergy to dairy products including cows' milk, butter, cheese and yoghurt. To provide protein in his diet dairy products were taken intentionally occasionally and taken unintentionally on many occasions by eating hotel/processed foods when away on business. On these occasions symptoms included gross bloating with waist size increasing by between 3 inches and 6 inches (7.5 cm and 15 cm), diarrhoea, reduced bowel transit time and increased bowel frequency. A regime of two tablets (100 mg sodium cromoglycate per tablet) taken with water half an hour before meals has completely blocked the reaction and resulted in bowel frequency returning to once daily, consistency of stools returned to normal and bloating prevented even when eating foodstuffs to which he was sensitive. They produce no feeling of discomfort and, since taking the tablets, his waist circumference has dropped from 44" (112 cm) to 36" (92 cm). A more varied diet may also now be eaten.

REFERENCES (CONCERNING PROPERTIES OF THE GUT)

Fimmel C J, Etienne A, Cilluffo T, et al. Long-term ambulatory gastric pH monitoring: validation of a new method and effect of $H_2$-antagonists. Gastroenterology 1985; 88: 1842-1851.

Prewett E J, Smith J T, Nwokolo C U, et al. Twenty-four hour intragastric acidity and plasma gastrin concentration profiles in female and male subjects. Clinical Science 1991; 80:619-624.

The Stomach. Eds S Gustavsson, D Kumar, D Y Graham. Churchill Livingstone—London 1992.

Malagelada J-R, Longstreth G F, Summerskill W H J & Go V L W. Measurement of gastric functions during digestion of ordinary solid meals in man. Gastroenterology 1976; 70: 203-210.

Malagelada J-R. Quantification of gastric solid-liquid discrimination during digestion of ordinary meals. Gastroenterology 1977; 72: 1264-1267.

Fordtran J S & Locklear T W. Ionic constituents and osmolality of gastric and small-intestinal fluids after eating. American Journal of Digestive Diseases 1966; 11:503-521.

Miller L J, Malagelada J-R & Go V L W. Postprandial duodenal function in man. Gut 1978; 19: 699-706.

Johansson C, Lagerlöf H O & Ekelund K. Intestinal flow rates and mean transit times and their relation to gastric emptying. The Mount Sinai Journal of Medicine 1976; 43: 58-67.

Johansson C. Absorption of sugar, fat, and protein in the upper intestine in relation to loads, transit times and the endogenous dilution. The Mount Sinai Journal of Medicine 1976; 43: 73-83.

Horowitz M, Maddern G J, Chatterton B E et al. Changes in gastric emptying rates with age. Clinical Science 1984; 67: 213-218.

The invention claimed is:

1. An oral drug delivery composition comprising a chromone wherein (1) not more than 10% of the chromone dissolves after two hours exposure of the composition to simulated gastric fluid and (2) at least 15% of the chromone dissolves within 10 minutes of subsequent exposure of the composition to simulated intestinal fluid, said composition further comprising disintegrant at a ratio of at least 1.2:1 (w:w) of disintegrant to chromone wherein said disintegrant is selected from the group consisting of microcrystalline cellulose, croscarmellose sodium, crosprovidone, sodium starch glycolate, and combinations thereof.

2. A composition according to claim 1 wherein the composition is formulated as a tablet.

3. A composition according to claim 2 wherein the tablet has an enteric coating.

4. A composition according to claim 2 wherein the composition is still in the form of a tablet at the end of the exposure of the composition to gastric fluid.

5. The composition claim 2 wherein the tablet comprises between about 50 mg and 200 mg of chromone.

6. A composition according to claim 1 wherein the composition comprises substantially spherical pellets of up to 5 mm diameter comprising the chromone, each pellet having an enteric coating.

7. A composition according to claim 1 wherein the ratio of disintegrant to chromone is between about 1.5:1 and 2.5:1.

8. A composition according to claim 1 wherein the disintegrant is microcrystalline cellulose.

9. A composition according to any one of the preceding claims further comprising an amphoteric surfactant or a surfactant having a hydrophile-lipophile balance (HLB) value of less than about 10.

10. A composition according to claim 1 wherein the chromone is sodium cromoglycate.

11. An oral drug delivery composition comprising a chromone wherein (1) not more than 10% of the chromone dissolves after two hours exposure of the composition to simulated gastric fluid, and (2) at least about 80% of the chromone dissolves within about 5 minutes of subsequent exposure of the composition to simulated intestinal fluid, said composition further comprising microcrystalline cellulose at a ratio of at least 1.4:1 (w:w) of microcrystalline cellulose to chromone.

12. An oral drug delivery composition comprising a chromone wherein (1) not more than 10% of the chromone dissolves after two hours exposure of the composition to simulated gastric fluid, and (2) at least about 27% of the chromone dissolves within about 10 minutes of subsequent exposure of the composition to simulated intestinal fluid, said composition further comprising disintegrant at a ratio of at least 1.2:1 (w:w) of disintegrant to chromone, wherein said disintegrant is selected from the group consisting of croscarmellose sodium, crosprovidone, sodium starch glycolate, and a blend of croscarmellose sodium and microcrystalline cellulose at a ratio of about 1:9 (w:w) of croscarmellose sodium to microcrystalline cellulose.

13. An oral drug delivery composition comprising a chromone wherein (1) not more than 10% of the chromone dissolves after two hours exposure of the composition to simulated gastric fluid, and (2) at least about 21% of the chromone dissolves within about 5 minutes of subsequent exposure of the composition to simulated intestinal fluid, said composition further comprising disintegrant at a ratio of at least 1.4:1 (w:w) of disintegrant to chromone, wherein said disintegrant is selected from the group consisting of super disintegrants in the form of a cross-linked cellulose, a cross-linked polymer, a cross-linked starch, and microcrystalline cellulose.

* * * * *